(12) United States Patent
Dholakia et al.

(10) Patent No.: US 8,080,399 B2
(45) Date of Patent: Dec. 20, 2011

(54) PHOTOPORATION OF CELLS

(75) Inventors: Kishan Dholakia, Glasgow (GB);
Christian Thomas Alcuin Brown, Glasgow (GB); Lynn Paterson, Glasgow (GB)

(73) Assignee: The University of Court of the University of St. Andrews, St. Andrews (GB)

( * ) Notice: Subject to any disclaimer, the term of this patent is extended or adjusted under 35 U.S.C. 154(b) by 860 days.

(21) Appl. No.: 11/720,488

(22) PCT Filed: Nov. 29, 2005

(86) PCT No.: PCT/GB2005/004569
§ 371 (c)(1),
(2), (4) Date: Sep. 11, 2007

(87) PCT Pub. No.: WO2006/059084
PCT Pub. Date: Jun. 8, 2006

(65) Prior Publication Data
US 2008/0274529 A1 Nov. 6, 2008

(30) Foreign Application Priority Data
Nov. 30, 2004 (GB) .................................. 0426182.2

(51) Int. Cl.
*C12N 13/00* (2006.01)
(52) U.S. Cl. ............... 435/173.5; 435/173.1; 435/173.4; 435/455; 435/460; 435/468; 435/471
(58) Field of Classification Search ................... 435/455, 435/460, 468, 471, 173.1, 173.4, 173.5
See application file for complete search history.

(56) References Cited

U.S. PATENT DOCUMENTS

| 5,246,437 | A | 9/1993 | Abela | |
|---|---|---|---|---|
| 5,330,467 | A | 7/1994 | Abela | |
| 5,795,755 | A | 8/1998 | Lemelson | |
| 2002/0019052 | A1* | 2/2002 | Nolan et al. | 435/461 |
| 2003/0147966 | A1* | 8/2003 | Franzen et al. | 424/491 |

FOREIGN PATENT DOCUMENTS

| DE | 198 27 957 | 12/1999 |
|---|---|---|
| EP | 0 843 198 | 5/1998 |
| EP | 1 225 221 | 7/2002 |
| WO | WO-92/06185 | 4/1992 |

OTHER PUBLICATIONS

Schneckenburger, H et al. Laser-assisted optoporation of single cells. Journal of Biomedical Optics. 2002. 7(3): 410-416.*
Arlt, J et al. Optical micromanipulation using a Bessel light beam. Optics Communications. 2001. 197: 239-245.*
Palumbo, G et al. Targeted gene transfer in eucaryotic cells by dye-assisted laser optoporation. Journal of Photochemistry and Photobiology B: Biology. 1996. 36: 41-46.*
Seeger, S et al. Application of laser optical tweezers in immunology and molecular genetics. Cytometry. 1991. 12: 497-504.*
Buer, C S et al. Insertion of microscopic objects through plant cell walls using laser microsurgery. Biotechnology and Bioengineering. 1998. 60(3): 348-355.*
Giuseppe Palumbo, et al; *Targeted gene transfer in eucaryotic cells by dye-assisted laser optoporation*; Journal of Photochemistry and Photobiology B: Biology; 1996; pp. 41-46; vol. 36; Elsevier Science S.A. (XP002939023).
Herbert Schneckenburger, et al; *Laser-assisted optoporation of single cells*; Journal of Biomedical Optics; Jul. 2002; pp. 410-416; vol. 7, No. 3 (XP008060521).
Paul Prentice, et al; *Membrane disruption by optically controlled microbubble cavitation*; Nature Physics; Nov. 2005; pp. 107-110; vol. 1; Nature Publishing Group (XP08060528).
B. Agate, et al; *Transfection of cells using a violet diode laser for photoporation*; 2005 Conference on Lasers and Electro-Optics Europe; p. 634; 2005 IEEE (XP010880264).
International Search Report for International Application No. PCT/GB2005/004569 completed Feb. 22, 2006.

* cited by examiner

*Primary Examiner* — Allison Ford
*Assistant Examiner* — Susan E Fernandez
(74) *Attorney, Agent, or Firm* — Alston and Birch LLP

(57) ABSTRACT

An opening is formed in a cell using laser radiation. A Bessel beam is formed using the laser radiation and the Bessel beam is directed onto the cell to form an opening. The guiding of material towards the opening may be involved using optical trapping/manipulation. The material may change cellular function or analyse cell behaviour. Both pulsed laser radiation and continuous wave radiation may be formed using the same laser.

13 Claims, 4 Drawing Sheets

| Central maximum diameter (equivalent Gaussian spot size) | Diffraction free propagation distance (Gaussian confocal parameter) |
|---|---|
| 1μm (330nm) | 0.33mm (0.0017mm) |
| 1.5μm (500nm) | 0.75mm (0.0040mm) |
| 2μm (660nm) | 1.33mm (0.0068mm) |
| 3μm (1μm) | 3.0mm (0.016mm) |

Figure 6

PHOTOPORATION OF CELLS

The present invention relates to a method for introducing material into a cell using a laser to form an initial opening, sometimes referred to as optoporation or photoporation.

The introduction of foreign including DNA, messenger-RNA, proteins, nano-particles and other biological and chemical macromolecules into cells is an essential procedure in a wide range of biological and medical experiments. By allowing such material to pass into a cell, many cellular processes may be altered and the behaviour of cells analysed. As an example when gene-bearing material from outwith the cell passes through the cell wall and is taken up, subsequent cell division passes on this new genetic information enabling the function of the cell to be manipulated. Various methods for puncturing cell membranes without causing any collateral damage have been proposed, for example chemical transfection. More recently, beams of light have been used to puncture the cell surface. This process is known as optical transfection, optical poration, photoporation or optical micro-injection.

Laser assisted optoporation has been demonstrated using lasers such as a continuous wave argon laser (488 nm), pulsed Nd:YAG lasers (1064 nm, 355 nm, or 532 nm) and more recently with the use of femtosecond pulsed, near infrared titanium-sapphire lasers. With most known arrangements the spot sizes that are used to open holes in the cell membrane have to be very small. Typically the laser has to be focused to a spot size of ~500 nm giving a full beam diameter of ~1.5 µm. This is a problem because when focusing to such a small spot size, the cell membrane must be very carefully positioned to coincide with the focussed spot of the laser, as shown in FIG. 1. For standard Gaussian beams, this is particularly problematic because the beam diverges significantly, as shown in FIG. 2, and the smaller the focussed spot size, the more quickly the light diverges on either side of the focal point. For radiation having a wavelength of about 400 nm, to achieve the required spot size, the incident beam has to be focused on the cell surface with an accuracy of the order of a few tens of microns, at the most. Where femtosecond radiation is used the location of the focus becomes even more critical and the focussed spot and the cell membrane must be co-located with a typical precision of <1 µm. This requirement for the femtosecond laser arises as a non-linear optical process, which is dependent on intensity, is used to form the opening in the cell membrane. Whilst it is possible to adjust samples to this level of accuracy, it is difficult and requires readjustment between each cell. This is a very labour intensive process. Another problem with known photoporation arrangements is that many require large and cumbersome lasers, for example argon ion lasers, or femtosecond lasers operated with higher power requirements.

According to one aspect of the present invention, there is provided a method for forming an opening in a cell using laser radiation, the method comprising forming a Bessel beam using the laser radiation and directing the Bessel beam onto the cell.

Bessel beams are made up from a central maximum surrounded by a set of rings with increasing radius. Over a long range, the central maximum of a Bessel beam does not undergo diffraction. This removes any of the beam spreading effects associated with Gaussian beams. Hence, by using a Bessel beam, a relatively small spot size can be achieved over a relatively long beam path. This means that the problem of focusing the spot on the cell is significantly reduced. A further property of the Bessel beam is that if obstructed, the beam can re-form after a finite distance following the obstacle. This can permit processing of multiple objects using a single Bessel beam. By contrast, a Gaussian beam is scattered following an obstacle and cannot be reformed.

Prior to optical micro-injection through an opening in the cell, the method may further involve trapping material and guiding it towards the cell. Such material could include, for example DNA, messenger-RNA, proteins, other biological and chemical macromolecules, and nano-particles, such as gold nano-particles and nano-particles that are functionalised with chemical materials of interest to change cellular function or analyse cell behaviour.

Optical trapping of particles allows for the concentration and localisation of materials of interest. This can be done using either a Gaussian or a Bessel light beam. Such optical trapping and concentration allows higher concentrations of materials to be directed into the cell under study. Typically, continuous wave radiation is used for trapping the material, and pulsed wave radiation is used to form the opening in the cell. Preferably, a single laser source is used for trapping and poration, the laser source being operable in a continuous wave mode for trapping and a pulsed wave mode for poration. Furthermore, in this mode of operation, the continuous wave laser can be used to trap and manipulate the cell that will be porated. The laser beam is then switched to pulsed, typically femtosecond, operation and optical poration takes place. Subsequently the laser can be switched back to continuous wave operation and the cell can be further manipulated by the laser beam without causing optical poration.

According to another aspect of the invention, there is provided a method comprising using laser radiation in a pulsed mode to form an opening through a cell wall and using the same laser in a continuous wave mode for optically trapping/manipulating the cell and/or material for injection into the cell.

According to yet another aspect of the present invention, there is provided a method for forming an opening in a cell comprising providing a blue/violet laser diode and directing continuous light from the blue laser diode onto the cell. Preferably, the blue laser diode output is formed into a Bessel beam Blue laser diodes are easy to use and relatively inexpensive. Using these opens the door to allow photoporation to move from academic study into the realm of practical devices. In particular, conventional microscopes could be readily adapted to include a blue laser diode photoporation system, thereby allowing this technology to become widely accessible.

Various aspects of the invention will now be described by way of example only and with reference to the accompanying drawings, of which:

FIG. 6 is a table showing comparative results for a Bessel beam and a Guassian beam.

Figure 1:
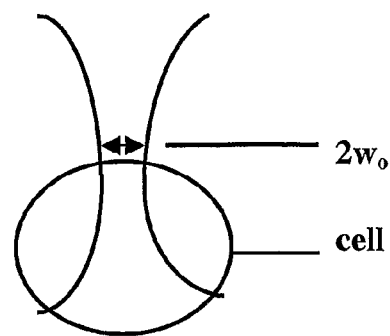
FIG. 1 is an illustration of a cell membrane positioned to coincide with the focused spot of a laser.
Figure 2:
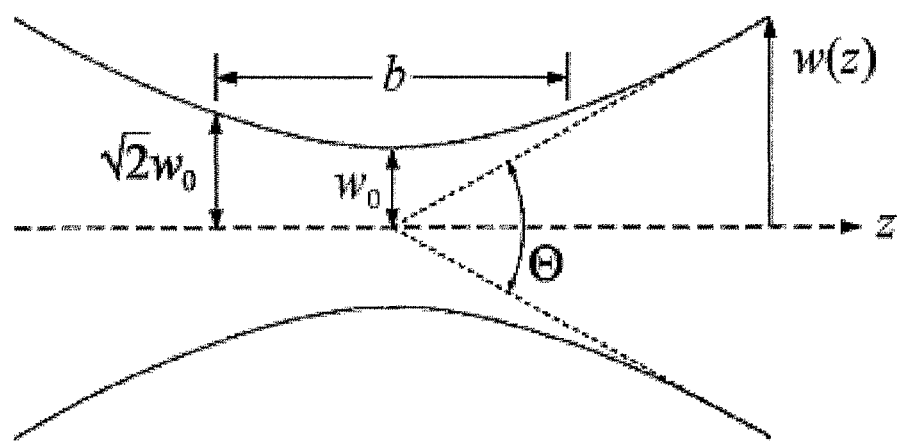
FIG. 2 is an illustration of the beam divergence of a standard Gaussian beam.
Figure 3:
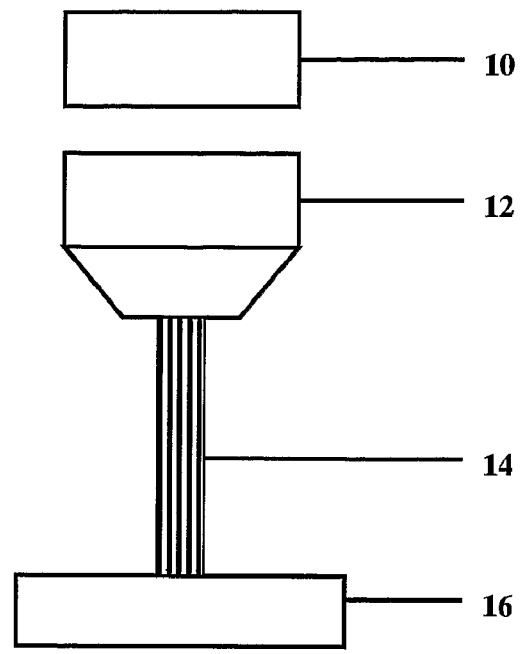
FIG. 3 is a block diagram of an optical poration system.

FIG. 3 shows an optical poration system that has a blue/violet diode laser 10 and an axicon 12 for forming a Bessel beam 14 at the output of the diode 10. By blue/violet, it is generally meant light having a wavelength in the range of about 390 nm to 500 nm. The diode laser 10 is positioned so that its output is directed onto a cell sample stage 16. A shutter is placed in the laser beam to allow the cell to be exposed to different durations of laser light. This exposure time can vary from 1 ms to full exposure from an open shutter. Typical exposure times are of the order of 30 ms. The power and spot size of the laser 10 are selected depending on the cells that are to be porated. In practice, it has been found that poration can occur for a 30 ms pulse of laser output of only 300 microwatts of power in a beam spot area of around 1 micron squared. At this level, it is possible to form an opening in many cell types.

Once an opening in the cell is formed, DNA or any other desired material can be introduced into the cell. The opening is then allowed to repair itself, without causing any visible damage thereto. Any material of interest could be introduced into the cell, for example gold nano-particles and nano-particles that are functionalised with chemical materials of interest to change cellular function or analyse cell behaviour. Injection of this material may be done using optical trapping and guiding. This would allow for the concentration and localisation of materials of interest. This can be done using either a Gaussian or a Bessel light beam. Typically, continuous wave radiation would be used for trapping, and pulsed wave radiation would be used to form the opening in the cell. In practice, the same laser source could be used for trapping and poration, although this is not essential. Techniques for optical trapping are known and so will not be described herein in detail.

Figure 4:
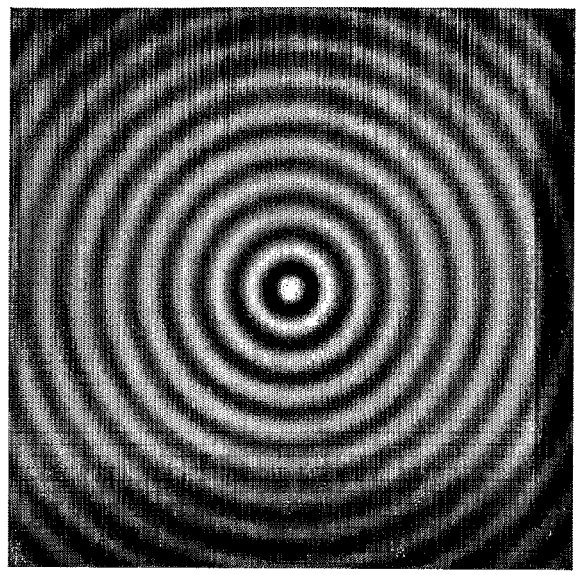
FIG. 4 is a photograph of a Bessel beam.
Figure 5:
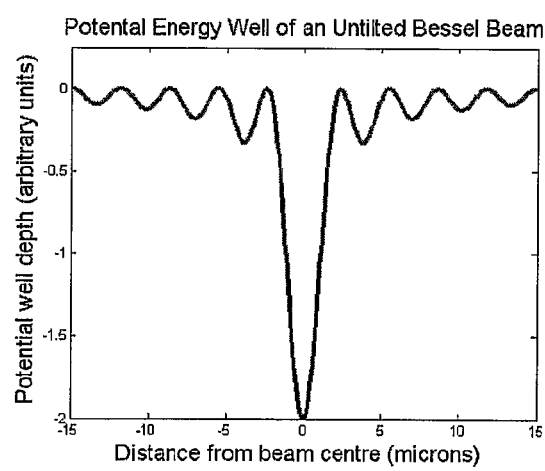
FIG. 5 is a plot of potential well depth versus distance from the centre for a Bessel beam.

FIGS. 4 and 5 show the Bessel beam that is output by the system of FIG. 3. This is made up from a central maximum surrounded by a set of rings with increasing radius. Over a long range, the central maximum of the Bessel Beam does not undergo diffraction. As an example, a typical Bessel Beam has a central maximum diameter of ~30 µm with a diffraction-free propagation distance of 0.3 m. This is significantly better than for a corresponding Gaussian beam.

To illustrate the advantages of a Bessel beam over a Gaussian beam, FIG. 6 shows a table giving the approximation for central maximum width and diffraction free propagation distance for a Bessel beam, with the equivalent Gaussian spot size given in brackets. It can be seen from this that the diffraction free propagation distance for a Bessel beam is 190× longer that the equivalent Gaussian beam. Hence, using a Bessel beam reduces any of the beam spreading effects associated with Gaussian beams, thereby reducing alignment problems. In addition, using a Bessel beam opens the way for photoporating arrays of cells and other biological materials that are being simultaneously trapped and/or guided by the Bessel beam due to the reconstruction behaviour of this type of laser beam, which has been previously demonstrated to manipulate arrays of cells.

The method in which the present invention is embodied uses the non-diffracting properties of a Bessel beam to perform photoporation in cellular and other biological materials with much reduced focussing and positional adjustments. This technique can be advantageously used with all wavelengths of electromagnetic radiation, and in all temporal regimes from continuous wave to attosecond pulses. Furthermore, using Bessel beams opens the way for photoporating arrays of cells and other biological materials that are being simultaneously trapped and/or guided by the Bessel beam. This significantly increases the scope for the manipulation and control of biological material. By using a blue laser diode as the radiation source, the practical applications for this methodology are significantly increased.

A skilled person will appreciate that variations of the disclosed arrangements are possible without departing from the invention. For example, whilst a laser diode is described as being the radiation source, it will be appreciated that any suitable laser could be used. Accordingly the above description of the specific embodiment is made by way of example only and not for the purposes of limitation. It will be clear to the skilled person that minor modifications may be made without significant changes to the operation described.

The invention claimed is:

1. A method for forming an opening in a cell using laser radiation, the method comprising forming a Bessel beam using the laser radiation; directing the Bessel beam onto the cell and using it to form an opening.

2. A method as claimed in claim 1 involving guiding material towards the opening using optical trapping/manipulation.

3. A method as claimed in claim 2 wherein the material is configured to change cellular function or to enable analysis of cellular behavior.

4. A method as claimed in claim 3 wherein the material comprises nano-particles that are functionalised with chemical materials.

5. A method as claimed in claim 4, wherein the nano-particles are gold nano-particles.

6. A method as claimed in claim 1, further comprising optically trapping or manipulating the cell before and/or after formation of the opening.

7. A method as claimed in claim 1 wherein the opening is formed using pulsed laser radiation to form the Bessel beam.

8. A method as claimed in claim 1, further comprising optically trapping or manipulating the cell before and/or after formation of the opening, wherein the optical trapping/manipulation is done using continuous wave radiation.

9. A method as claimed in claim 8, wherein the opening is formed using pulsed laser radiation to form the Bessel beam, and wherein the same laser is further used for doing the trapping/manipulating.

10. A method as claimed in claim 1 wherein the laser radiation comprises blue/violet radiation.

11. A method as claimed in claim 1 involving using a laser diode as the radiation source.

12. A method as claimed in claim 1, further comprising guiding material towards the opening by optical trapping/manipulation using continuous wave radiation.

13. A method as claimed in claim 12, wherein the opening is formed using pulsed laser radiation to form the Bessel beam, and wherein the same laser is further used for doing the trapping/manipulating.

* * * * *